United States Patent [19]

Laboureau et al.

[11] Patent Number: 5,112,335
[45] Date of Patent: May 12, 1992

[54] INSTRUMENT FOR MARKING AND DRILLING FEMORAL AND TIBIAL INSERTION TUNNELS

[76] Inventors: Jacques-Philippe Laboureau, 24, rue Fontaine Billenois; Alain Cazenave, 22bis, rue du Docteur Calmette, both of 21000 Dijon, France

[21] Appl. No.: 550,618

[22] Filed: Jul. 10, 1990

[30] Foreign Application Priority Data

Jul. 11, 1989 [FR] France .................. 89 09325

[51] Int. Cl.⁵ .............................................. A61F 2/32
[52] U.S. Cl. ........................................ 606/88; 606/96; 606/102
[58] Field of Search ............... 606/86, 87, 88, 89, 606/96, 97, 98, 102

[56] References Cited

U.S. PATENT DOCUMENTS

| 2,200,120 | 5/1940 | Nauth | 606/96 |
|---|---|---|---|
| 2,235,419 | 3/1941 | Callahan | 606/96 |
| 4,708,139 | 11/1987 | Dunbar | 606/96 |
| 4,739,751 | 4/1988 | Sapega | 606/96 |
| 4,781,182 | 11/1988 | Purnell | 606/96 |
| 4,813,407 | 3/1989 | Vogen | 606/86 |
| 4,883,048 | 11/1989 | Purnell | 606/96 |
| 4,920,958 | 5/1990 | Walt | 606/96 |
| 4,945,904 | 8/1990 | Bolton | 606/96 |

FOREIGN PATENT DOCUMENTS

| 162027 | 11/1985 | European Pat. Off. . |
|---|---|---|
| 292678 | 11/1988 | European Pat. Off. . |
| 0151113 | 10/1937 | Fed. Rep. of Germany ........ 606/87 |
| 685364 | 12/1939 | Fed. Rep. of Germany . |

OTHER PUBLICATIONS

Copy of the French Search Report.

Primary Examiner—Robert A. Hafer
Assistant Examiner—Michael Brown
Attorney, Agent, or Firm—Sandler, Greenblum & Bernstein

[57] ABSTRACT

Surgical ancillary instrument for aiming and drilling of femoral and tibial insertion tunnels of at least one bundle of neo-ligaments for the reconstruction of the anterior opposite ligament of the knee. The instrument includes a handle equipped at one of its ends with a straight rod finishing in a hook perpendicular to the rod serving as a reference for at least one aimer barrel having in relation to the rod predetermined horizontal and vertical directions so as to obtain an alignment of the drilling directions of the tibial and femoral insertion tunnels when the knee is in extension.

18 Claims, 3 Drawing Sheets

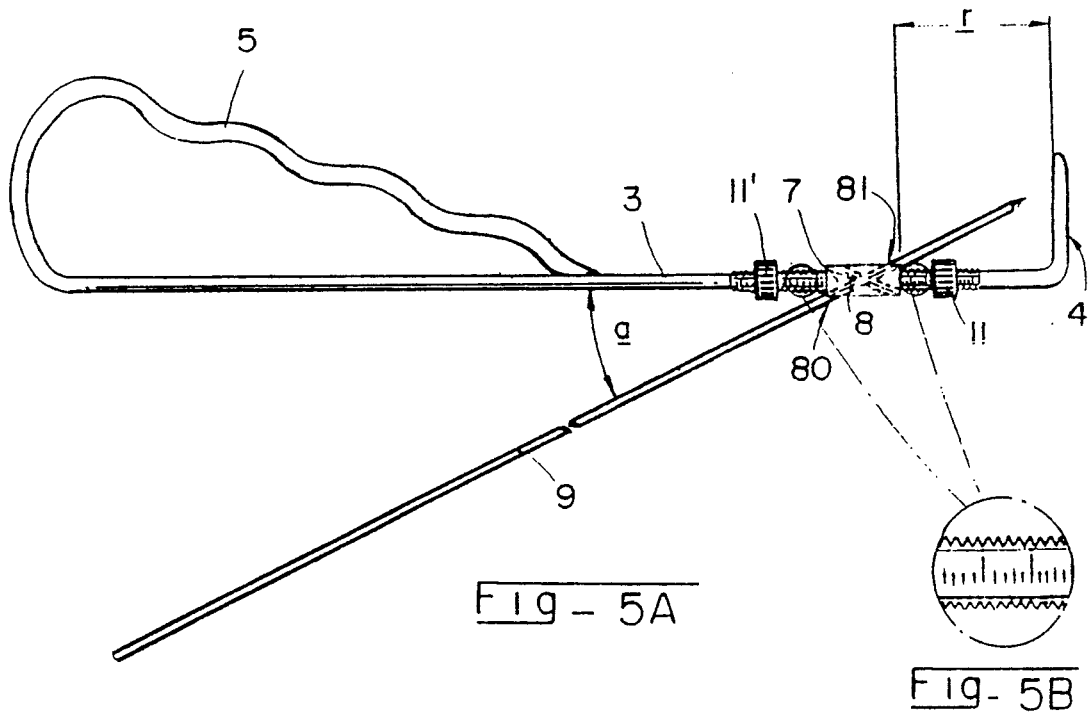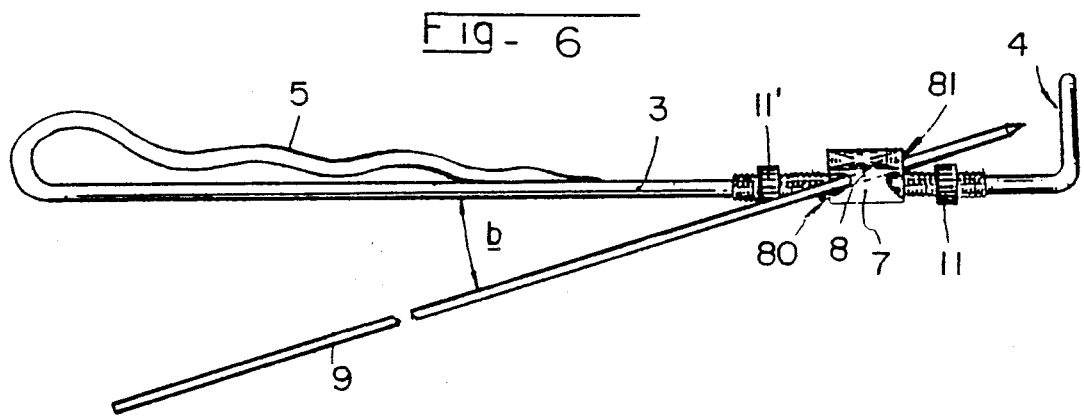

INSTRUMENT FOR MARKING AND DRILLING FEMORAL AND TIBIAL INSERTION TUNNELS

BACKGROUND OF THE INVENTION

1. Field of the Invention

This invention concerns a surgical ancillary instrument allowing the marking of the entrance hole to the femoral insertion tunnel of a neo ligament for the reconstruction of the anterior cruciate of the knee, in the total respect of its isometry, as well as the guiding of an instrument for the drilling of the same tunnel and beneficially allowing the guiding of an instrument for the drilling of a tibial insertion tunnel of the same neo-ligament.

2. Discussion of background and Relevant Information

The main problem encountered reconstructing the anterior cruciate of the knee is with respect to its isometry. By isometry, is meant the fact that the distance between the point of insertion of the ligament in the tibia and the point of insertion of the same ligament in the femur should not vary no matter what the degree of flexion or extension of the knee. Indeed, it can be imagined that if this isometry were not respected, there would be a lack of stability in the positions where the ligament is relaxed and, on the contrary, a limitation of mobility if, in a certain position the ligament were submitted to an excessive tension.

Generally speaking, the tibial insertion of the ligament is easily found considering its very anterior position on the tibial plateau. It is not the same for the femoral insertion which is carried out on the axial side of the external femoral condyle within a deep seated area, difficult to see directly by the surgeon. This femoral insertion area also greatly varies from one person to another and the choice of this point is usually left for the surgeon to appreciate. Moreover, it is important to plan when implanting a prosthetic ligament of knee, a the perfect alignment of the longitudinal axes of the tibial and femoral insertion tunnels so that, the knee being in its extension position, the prosthetic ligament is straight so as to avoid all the useless efforts due to raised edges of the insertion tunnels.

The main object of this invention is therefore to offer the realization of a surgical instrument for marking with precision, in accordance to criteria capable of being measured and reproduced, the position of the hole at the entrance to the femoral insertion tunnel at the external condyle level.

In this respect, a number of drilling guides are known, but these guides allow insertion tunnels to be chosen between two points chosen at will depending on the surgeons experience. None of these guides at present allow to determine with precision the isometrical point which however is the compulsory point of entry to the neo-ligament, if a perfect isometry is required. Anatomical works, carried out amongst others by inventors, have enabled to establish with certainty that the far posterior part of the external femoral condyle actually corresponds to the quadrant of a perfect circle, the radius of which varies, depending on the person concerned. These same works have also enabled to determine that the geometrical center of this circle corresponded exactly to the sought isometric point. The location of this isometric point can therefore be determined in relation to its distance to the far edge of the condyle, insofar as it can be measured.

As of then, it is just necessary, prior to the operation, to practically determine the center of the circle mentioned above: namely by measuring its distance in relation to the rear edge of the condyle. It is well known how to take such a measurement from an X-ray without an enlargment by using teleradiography, for example. It would then be sufficient to superimpose transparent tracings to measure directly the radius of the circle corresponding to the posterior part of the femoral condyle and to deduce its center. From this same center it is easy to draw a line parallel to the bottom of the intercondyloid notch by marking, for example, the Blumensatt line, which is a well known radiological reference. This line corresponds exactly to the ideal axis of the femoral insertion tunnel in the reconstruction of the anterior cruciate of the knee. Finally, it is sufficient to note the distance thus measured on an appropriate instrument equipped with a display, taking reference on the posterior edge of the external condyle to obtain, with excellent precision, the isometric point of femoral insertion of the neo-ligament during the operation.

SUMMARY OF THE INVENTION

One of the objects of this invention is therefore to offer a surgical ancillary instrument for marking of the femoral insertion tunnel of a neo-ligament, for the reconstruction of the anterior cruciate of the knee, well the intercondyloid entry to the tunnel being located at the isometric point coinciding with the center of the circle corresponding to the posterior edge of the femoral condyle, and for drilling of the tunnel according to a direction such that in the extension position of the knee, the extension of the tunnel is within the tibial insertion tunnel axis, the instrument according to the invention includes, a rod at its near end, a handle, and at its far end a hook curved at a right angle, coming across the inter-condyloid not bearing on the posterior edge of the femoral condyle concerned, to obtain a positioning reference with an aimer and a guide linked to the, rod the instrument is characterized by the fact that the aimer, whose orientation is fixed according to horizontal and vertical directions, can be displaced in parallel to the rod over a graduated section to be brought to a stop by suitable means, so that the distance between the condyloid bearing surface of the hook and the point of intersection between the drilling direction and the rod is equal to the radius of the quadrant of the circle, the center of which is the isometric point previously determined, for example, by teleradiography.

From such an ancillary instrument, a surgeon can determine, with precision the position of the femoral insertion isometric point of the neo-ligament. During an operation, in which the surgeon has chosen, for example, the endo-articular way, with the knee to be operated being in a position such that the femoral axis is almost at 90° in relation to tibial axis, the operator initially introduces the rod of the instrument according to the invention, in the intercondyloid notch, until the distal part of the rod, curved according to a right angle, like a hook, comes to rest on the posterior edge of an external condyle of the femur. When this curved part rests correctly on the posterior part of the condyle, the operator is then in a position such that the axis of the rod supporting the bent part coincides with the direction of the radius of the circle quadrant made of the posterior part of the said condyle. Under these conditions, it is sufficient to move the tibial aimer along the rod, of a value equal to the radius of the circle of the posterior part of the condyle, to thereby position it on the intra-articular anterior side of the femur at a point corresponding to the insertion isometric point. Starting from this point, the aimer barrel will be used directly or by means of guiding adjustable calibrated bushes, with one pin as a guide for a pin which will be introduced according to the direction of the same aimer, so as to guide the drilling of a femoral insertion tunnel, for example by means of a classical drill including a central conduit allowing its sliding along the positioning pin.

It is therefore quite evident that the ancillary instrument, apart from its longitudinal micrometric adjustment possibilities, allowing to position the aimer, as we have just seen, under normal operative conditions, by means of a range of vertical and horizontal inclinations in relation to the plane composed by the rod on one hand, its curved distal part on the other hand, an exact positioning to the pins and drills to consider other requirements in the ligamentary reconstruction; these are namely the intra-osseous tunnel directions, in this case tibial or femoral insertion tunnels which should be preferentially determined so that in the extension position of the knee, the prolongation of the transtibial and transfemoral tunnels are as close as possible to the straight line. In accordance with the secondary characteristics of the invention, it was planned to give special angular directions to the aimer axis, so as to obtain this alignment between the transtibial and transfemoral insertion tunnels when the knee is in the extension position.

In a special preferred version of the surgical ancillary instrument in accord once with the invention, it is planned to carry out the operation not through an endoarticular passage, but by means of the extra articular way which is preferably used in arthroscopic surgery. We know that in this case, the operation will be carried out from the outside of the knee which will avoid practicing deep incisions and allow the reconstruction of the ligaments according to a totally benign operation.

Under these conditions, the marking and the drilling of the femoral insertion tunnel is realized from the external cortical of the femur, to arrive in the intra-articular insertion zone, precisely at the isometric point of insertion. Since the isometric point of insertion would always be positioned starting from the posterior edge of the external femoral condyle which we now know corresponds to an almost perfect circle quadrant, the instrument in compliance with the invention's variant includes a rod equipped at its distal end with a hook curved at right angles identical to the rod detailed in the first variant of the information in compliance with the invention. The proximal end of the rod is equipped with a handle allowing its introduction in the intercondyloïd notch, and to move towards the outside of the knee, wela the whole instrument holding the aimer. This set, which is composed of a bar lying parallel to the first rod can slide through a tunnel made in the handle of the rod so that the aimer can move in parallel to the rod procuring the reference. Of course, micrometric means allow the control of the longitudinal movements of the aimer barrel and to longitudinally position the outlet of the barrel so as to bring it to an adequate point in the external cortical of the femur at the outlet of the femoral insertion tunnel passing through the isometric point. The aimer barrel is also placed in such a way that it presents a double vertical and horizontal slope to take into account the extra requirement already described for the previous version.

Indeed the instrument produced according to this second version and in accordance with the invention is used in the following way: the knee to be operated is presented in its bent position so that the surgeon can introduce the reference rod into the intra-articular space, until he can place the hook in the resting position on the posterior edge of the external condyle. It is then introduced into the adjustment tunnel at the end of the handle, a sliding bar holding at the end of the marking and guiding barrel, placed in such a way that the extension to its axis cuts the reference rod at an intersection point such that this point is at an exact distance from the bearing surface of the hook, equal to the value of the radius of the posterior edge of the external femoral condyle, previously measured in the conditions already mentioned (teleradiography for example). Finally, we should note that the sliding bar bearing at one of its ends the aimer cannon, presents a sufficient vertical slope so that the direction of the transfemoral tunnel obtained by drilling, thanks to the guiding of the aimer barrel, is in the axis of the transtibial tunnel direction when the knee is in total extension.

It should also be noted that some special revisions could complete the description that has just been made of this second version such as, for example, the possibility of mounting, inside the aimer barrel, bushes of various diameter, allowing the precise adjustment of the distance between the aimer barrel and the external part of the knee where the drilling of the insertion tunnel will be carried out. These bushes include on their inside a conduite acting as a guide for the pin used for positioning the drill. The bushes can be threaded so that they can be screwed into the inside of the aimer barrel and moved axially with great precision. Of course, equivalent solutions can be found suitably by making, for example, the length of the handle at the end of the reference rod vary, so as to adjust the distance between the rod and the sliding bar of the barrel, to take into account the anatomical differences of knees observed with each patient.

Finally, it is planned that in the conditions of operation by extra-articular means, the stroke of the drill crossing from the external part to the intra-articular insertion area be limited when the tunnel is totally perforated so as not to cause unnecessary injuries. For this, there is a concavity in the vertical plane of the reference rod liable to form a stop for the sharp end of the drill, without allowing it to scrape, so as to avoid any injury to the surrounding mass.

It is quite clear, even if this solution is not generally retained today by praclitioners, that it would be easy to implant a new ligament with two bundles, posteroexternal and antero-internal, to reconstruct the original ligamentary system more faithfully. For this it would again be necessary to find the isometric point of the articulation and to double the aimer barrel so as to carry out the drilling of two femoral tunnels, so that they are divided on either side of the isometric point, according to a line between centers, making an angle of approximately 45° with the vertical, to respect the femoral anatomical insertion of the cruciate in a form of a beam centered on the same isometric point.

The second aim of the invention is to use at the utmost the ancillary instruments according to the invention as a guide for drilling a tibial insertion tunnel of which is easy to find the entrance on the tibial plateau when the operation takes place, whereby the longitudinal direction of this transtibial tunnel is always obtained empirically. Moreover, another object of the invention is therefore to describe a special adaptation of the version to carry out just one drilling correctly.

BRIEF DESCRIPTION OF THE DRAWINGS

The invention would be better understood and other advantages will come to light from the description that is to follow of the two versions of the surgical ancillary instrument in compliance with the invention given hereunder as an non limitative example, in reference to the drawings, in which:

FIG. 5 is a general view of the first version of the ancillary instrument in accordance with the invention shown in plane and equipped with its positioning pin.

FIG. 6 is a slight perspective of the ancillary instrument illustrated in FIG. 5 preferentially seen from the side.

Figure 1:
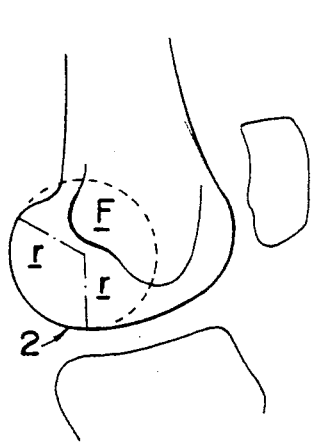
FIG. 1 shows a cross-sectional diagram of the articulation of the knee, on which have been shown the posterior area of the external femoral condyles, showing their circular form and the positionning of the corresponding geometrical centre.

In compliance with FIG. 1, we now know that the posterior part of the external femoral condyle shows a profile in the form of a circular quandrant, the center F of which can easily be found before the operation and the corresponding r radius can consequently be calculated. We also know that the centre F of the circle quandrant corresponds to the isometric point for the neo-ligament femoral insertion.

Figure 2:
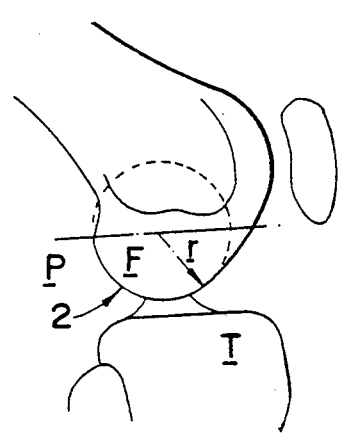
FIG. 2 shows a schematic drawing of the articulation of the knee, in intermediate position of flexion, showing the isometry of the neo-ligament, in showing that the FT distance remains constant in all the positions of the knee.

In this respect, FIG. 2 depicts the femoral and tibial part of the knee articulation showing that the FT distance between the points of femoral and tibial insertion remained constant, no matter what the angular position of the knee.

Figure 3:
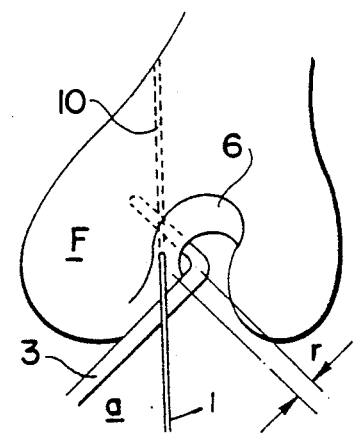
FIG. 3 is a schematic drawing of the top of the femur resting on its condyles, showing the reference rod of the instrument, according to the invention, in bearing position on the posterior side of the external condyle as well as the relative position of the isometric point composing the entrance to the femoral insertion tunnel.

With reference to FIGS. 5 and 6, the surgical ancillary instrument in compliance with the invention according to the first version corresponding to an endo-articular operation, includes a rod 3 also called hereunder "reference rod" having at his distal end a hook 4 bent at right angles on a sufficient distance to come and hook onto the posterior edge of the condyle 1. The rod 3 includes at its proximal end a handle 5 of suitable shape to allow the whole instrument to be taken hold of, and also to guide its penetration into the intercondyloid notch 6, in compliance with FIG. 3.

A cursor 7 can slide on the rod 3 between two positions separate from each other by about 3 cm from a stop on the light positioned at approximately 15 mm from the hook 4 bearing on the posterior edge 2 of the external condyle 1. The cursor 7 includes a tunnel 8 placed above the rod 3 and according to angular vertical and horizontal directions, defined hereafter. The tunnel 8 is first of all an aimer barrel meant to receive a pin 9 which realizes the isometric point F on the intraarticular surface of the condyle 1, which pin 9 will then be used to determine the direction of the drilling of the transfemoral insertion tunnel. In this version, reference numeral 8 to the drawing will either concern the aimer barrel or the tunnel which plays the same role.

So as to respect to all the requirements needed for the perfect reconstruction of the anterior cruciate, as we have already explained in detail in the introduction, tunnel 8 crossing the cursor 7 is such that its longitudinal axis presents in comparison with the horizontal plane determined by rod 3 and segment 4, an angular slope a, equal to approximately 20°, in the horizontal plane counted from the axis of rod 3, in the direction of the end of the segment 4, and a slope b, of about 40°, in the vertical plane, from a low point corresponding to the entrance 80 to the tunnel 8 to a high point corresponding to the outlet 81 of the same tunnel 8 opposite segment 4. The linear portion of rod 3, on which the cursor 7 can be freely moved, includes a micrometric graduation, such as represented on an enlargement in FIG. 5, allowing the exact positioning of the outlet 81 of tunnel 8, opposite segment 4, at an equal distance from radius r of the posterior surface of the condyle 1, previously measured by teleradiography, for example. The cursor 7 is then held in this position, for example, by means of two knurls 11 and 11' brought into contact on either side of the cursor 7 by means of a threading made for this purpose on rod 3. We can also note that in an extra feature of the invention, the said threading is beneficially machined to a pitch of 1/10th, allowing each of the threads to be used as a micrometric mark for the longitudinal positioning of the cursor 7.

The part of the rod 3 on which the cursor 7 can slide has a square section preventing the support 7 from any axial rotation around the rod 3. However, it should be noted that cursor 7 can be brought beyond the graduated area towards its proximal end to carry out the rotation of 180°, so that the instrument can be used by bearing on the posterior edge of the right or left condyle 1.

Figure 7:
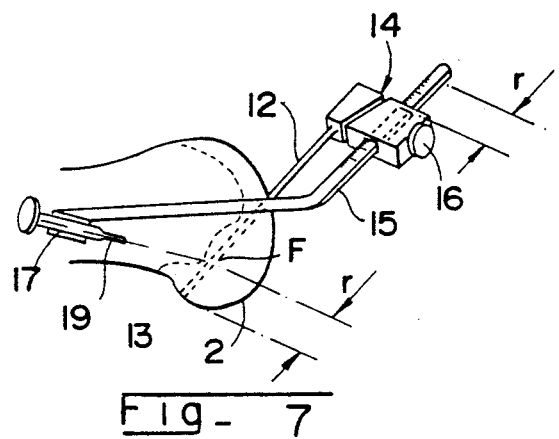
FIG. 7 is a perspective view of the second version of the ancillary instrument for the drilling of the trans-femoral tunnel showing the instrument in position on the external edge of the femoral condyle.
Figure 4:
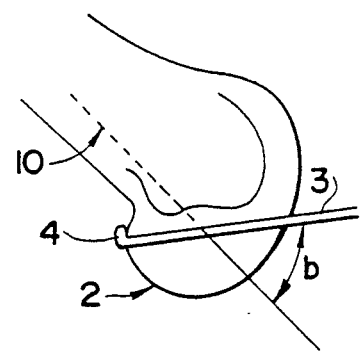
FIG. 4 is a schematic drawing in elevation of the external femoral condyle, showing the position of the reference rod of the instrument according to the invention, in bearing position on the posterior edge of the condyle as well as the relative position of the isometric point composing the entrance to the transfemoral insertion tunnel.
Figure 8:
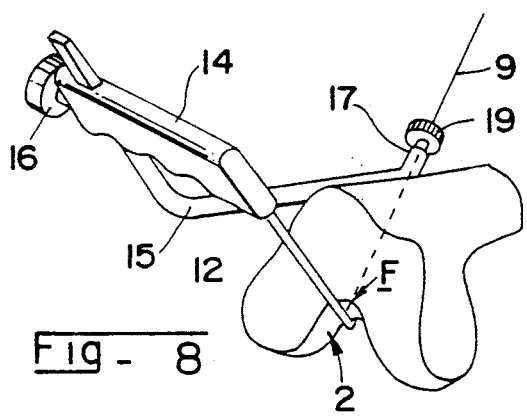
FIG. 8 is another perspective view of the version illustrated in FIG. 7 showing the instrument in position in the intercondyloid notch.
Figure 10:
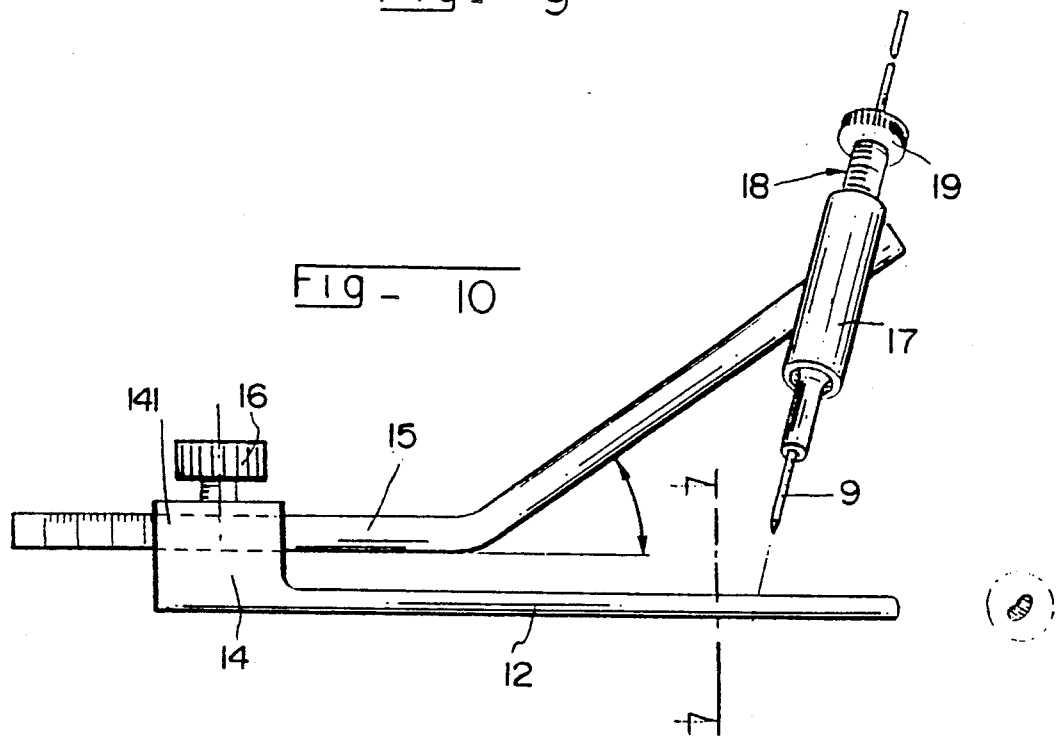
FIG. 10 is a schematic drawing of the instrument in FIG. 9 seen from the side illustrating a partial and enlarged figure of the transversal section of the reference rod of the instrument showing its concavity turned towards the aimer barrel outlet so that it can serve as a stop to the drill when it comes through the transfemoral insertion tunnel.

According to a second version of the surgical ancillary instrument in accordance with the invention, allowing the reconstruction of the anterior cruciate of the knee by extra-articular means usually carried out under arthroscopy. The special execution often preferred of the instrument is offered in accordance with FIGS. 7 and 10, with FIGS. 7 and 8 showing the instrument in a corresponding working position in relation to the femoral condyles.

The ancillary instrument is here composed of a first rod 12 including, as with rod 3 in the previous embodiment, at its distal end, a hook 13 curved to a right angle. This hook 13 is in all points identical to hook 4 of the previous embodiment. The rod 12 includes, at its proximal end, a handle 14 perpendicular to the axis of rod 12 and of a length much greater than the thickness of a femoral condyle. At the end of the handle 14, there is an axis tunnel 141 parallel to that of rod 12, through which slides a bar 15 which can be stopped by classical blocking screw 16. This bar 15 has, at its end opposite the handle 14, an aimer and guiding barrel 17 placed in such a way that the prolongation to its axis cuts the axis of the reference rod 12.

It should be pointed out here that the aimer and guiding barrel 17 should give the same results as those obtained in the first version by means of the pin 9 guided in the tunnel 8, apart from the fact that the drilling of the transfemoral tunnel is carried out in this version from the external cortical of the femur. The relative position of the aimer and guiding barrel 17 in comparison with the planes defined by the axis of the rod 12 and the axis of the segment 13, is deducted from a first horizontal angular slope r, equal to approximately 20°, and to a second angular slope upwards in the vertical plane, corresponding to an angle of 40°, the top of which coincides with the center of the tunnel in the handle 14 of the rod 12. The adjustment of the ancillary instrument in this embodiment is obtained by the sliding of the bar 15 supporting the aimer barrel 17 inside the guiding tunnel 18 provided at the end of the handle 14, this movement being carried out according to a direction substantially parallel to the axis of the reference rod 12. In this way, it is possible to graduate the proximal end of the bar 15, in such a way that the origin of this graduation corresponds to the position of the aimer cannon 17, such that the intersection point between prolongation of its axis and the reference rod axis coincides with the intersection of the rod 12 and the anterior surface of the hook 13. It thus appears that the difference between the bar 15 from this origin, for example with a value r, pre-established by the means described above will allow to obtain a transfemoral insertion tunnel, passing through the isometric point F of the condyle 2 in conditions identical to those obtained from the instrument in compliance with the first version. In an extra-feature, a threading inside the aimer barrel 17 has been provided, allowing bushes 19 of various sizes to be screwed in, and which can be moved longitudinally inside the aimer inside the barrel 17 just by screwing. It is easy to understand that the size of the femoral condyles can vary from one person to another, and therefore the length of the aimer barrel 17 should be adjusted to bring its end into contact with the external cortical of the femur. It is apparent that the longitudinal adjustment and the holding of the bushes 19 inside the aimer barrel 17 can be obtained by any other means such as, for example, by sliding with a transversal blocking screw without leaving the scope of the invention.

It should be noted that it was beneficially planned that the section of rod 12 be in concave form, turned towards the outside of the instrument, in such a way that the rod 12 may be used as a final stop to the drill when it comes through the transfemoral insertion tunnel, so as to avoid any unnecessary injury to the surrounding mass.

Figure 11:
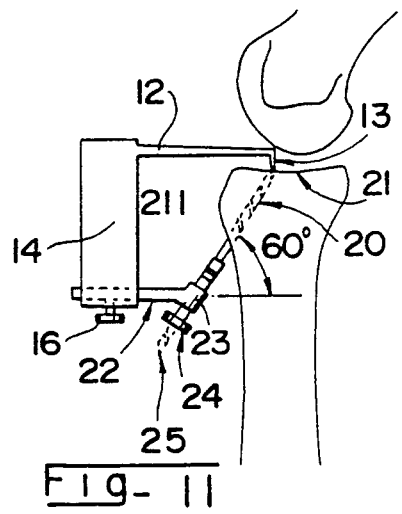
FIG. 11 shows an adaptation of the ancillary instrument for the drilling of the transtibial tunnel according to an ideal direction for fixing a neo-ligament.
Figure 9:
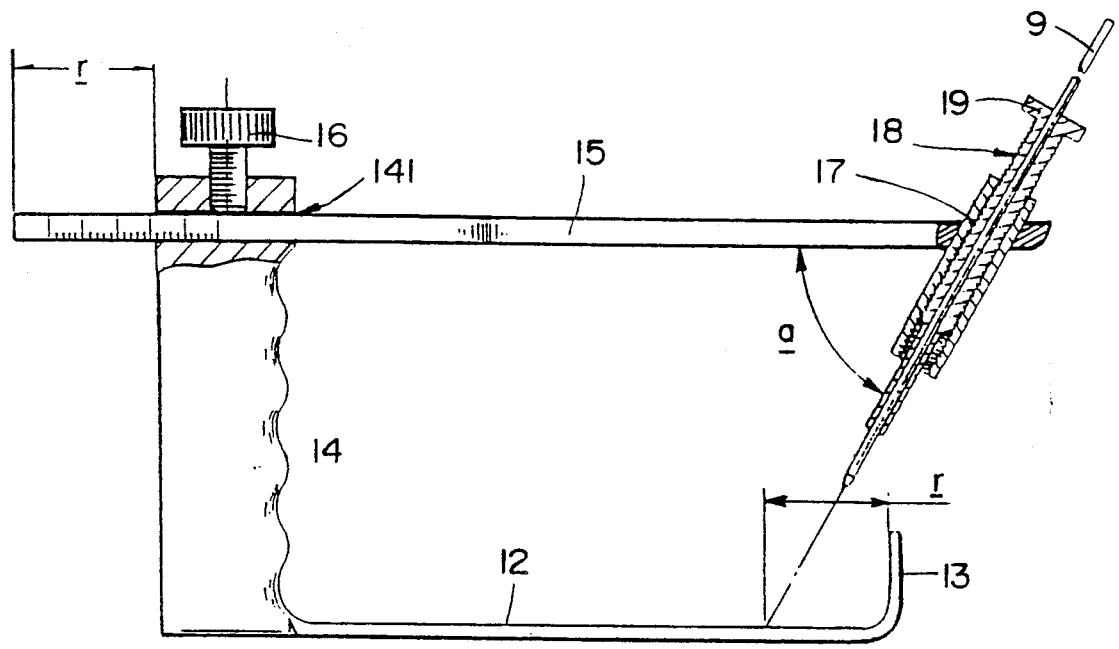
FIG. 9 is a schematic drawing of the second version of the ancillary instrument of FIGS. 7 and 8 in accordance with the invention shown in the plan.

A special adaptation of the second embodiment of the ancillary instrument according to the invention will now be described which allows the drilling of a transtibial tunnel 20, capable of receiving the new ligament from the tibial plateau 21, with reference to FIG. 11.

The adaptation mainly consists in the replacement of the sliding bar 15 equipping the ancillary instrument previously described by a new bar 22 bearing an aimer barrel 23 allowing directly or by means of a bush 24 the guiding of a drill 25 meant for the drilling of the transtibial tunnel 20.

It should be reminded first of all that the entrance 211 to the transtibial tunnel 20 on the tibial plateau 21 is quite visible by the operator when the knee is in bent position. The difficulty is therefore to realize the transtibial tunnel 20 according to the right direction, in such a way that the ligament, once placed in the two transtibial and transfemoral tunnels, follows as closely as possible a straight line when the knee is in extension. This direction of the transtibial canal, situated in the median plane of the tibia passing through the anterior peak of the same tibia, is such that it makes an angle close to 60° in comparison with the tibial plateau plane 21.

Consequently, we had to provide for the adaptation of the ancillary instrument a bar 22 that can slide in the handle 14 in the same way as the bar in the previous version, but the possibility of blocking thanks to the screw 16. As in the previous embodiment the bar 22 is straight and includes at its free end an aimer barrel 23 whose longitudinal axis makes an angle of 60° in comparison with the axis of bar 22. The aimer barrel 23 is, as in the previous embodiment, equipped inside with a bush 24 that can be moved longitudinally by means, for example, of a threading or any other means of displacement, including means of blocking in the required position. Under these conditions, when the bush 24 is brought into contact with the tibial cortical, the instrument being in the right position as it is explained hereafter, it is sufficient to pass inside the bush 24 a drill 25 to carry out the transtibial drilling 20.

In the order to do this, the instrument thus adapted, is used in the following way. The hook 13 at the end of the rod 12 having the handle 14, is placed by its point slightly backwards and inside the tibial insertion center of the anterior cruciate, and the handle 14 is itself held in such a way that it is parallel to the tibial pre-peak by the operator. Considering the angulation of the drill holder, it would seem that in these conditions, the tunnel will be realized to have a direction close to 60° in comparison with the tibia plateau. Of course, the position of bar 22 bearing the aimer barrel 23 should be blocked in a position such that the direction of the aimer barrel 23 passes by the end of the hook 13, born by the rod 12, so that the transtibial tunnel arrives in the insertion center 211 of the tibial plateau 21. Of course the drilling can be carried out either directly with drill 25 or after setting up a pin of the same type as pin 9 in the previous version, on which will be introduced later a longitudinally perforated bit.

Of course all these versions of secondary importance do not exceed the scope of this invention. The surgical ancillary instrument such as it has been described previously is namely applicable for the replacement of the anterior cruciate of the knee.

We claim:

1. Surgical ancillary instrument for marking and drilling of the femoral and tibial insertion tunnels of at least one bundle of neo-ligaments for the reconstruction of the anterior cruciate of the knee, said instrument comprising:

a straight rod having a distal end and a proximal end;

a handle at said proximal end;

a hook at said distal end, said hook being substantially perpendicular to said rod;

means including a passageway guidable along said rod on a graduated scale in relation to said hook for obtaining predetermined horizontal and vertical directions of said passageway to obtain an alignment of marking and drilling directions of the femur and tibial insertion tunnels when the knee is in extension based on a predetermined radius associated with the isometric point of a knee, and said means including a passageway include a cursor having a tunnel positioned therein, said tunnel having an inlet, an outlet and predetermined horizontal and vertical directions, said cursor being guidable along said graduated scale, means for stopping said cursor to obtain a distance between said outlet of said tunnel and said hook which is equal to a predetermined radius associated with the isometric point of a knee.

2. The instrument according to claim 1, wherein said means including a passageway is slidable parallel to said rod.

3. The instrument according to claim 1, wherein said means including a passageway is slidable along said rod.

4. The instrument according to claim 1, wherein said instrument is for marking of a femoral insertion tunnel of a neo-ligament for reconstruction of the anterior cruciate of a knee, with the inter-condyloid entrance to the femoral insertion tunnel being located at an isometric point coinciding with the center of a quadrant corresponding to the posterior edge of the femoral condyle, and for drilling said femoral insertion tunnel, according to a direction whereby in the extension position of the knee, the prolongation of the femoral insertion tunnel is almost in the axis of the tibial insertion tunnel, and said hook is adapted to come across the inter-condyloid notch to bear on the posterior edge of a femoral condyle, further including a means for stopping said means including a passageway in a predetermined position to obtain a distance between the condyloid bearing surface of said hook and a point of intersection of said passageway with said rod equal to a predetermined radius associated with the isometric point of a knee.

5. The instrument according to claim 1, wherein said predetermined horizontal and vertical positioning comprises an angular slope between said tunnel and said rod of about 20° in a horizontal plane passing through said rod and said hook, and an angular slope of about 40° in a vertical plane passing through said inlet and said outlet of said tunnel.

6. The instrument according to claim 1, wherein said rod is square at said graduated scale to prevent axial rotation of said cursor.

7. The instrument according to claim 6, wherein said graduated scale includes threads of a predetermined pitch.

8. The instrument according to claim 7, wherein longitudinal movement of said means for stopping is determined by said threads.

9. The instrument according to claim 7, wherein said means for stopping includes two stop screws, one positioned in front of said cursor and one behind said cursor.

10. Surgical ancillary instrument for marking and drilling of the femoral and tibial insertion tunnels of at least one bundle of neo-ligaments for the reconstruction of the anterior cruciate of the knee, said instrument comprising:

a straight rod having a distal end and a proximal end;

a handle at said proximal end;

a hook at said distal end, said hook being substantially perpendicular to said rod;

means including a passageway guidable along said rod in relation to said hook for obtaining predetermined horizontal and vertical directions of said passageway to obtain an alignment of marking and drilling directions of the femur and tibial insertion tunnels when the knee is in extension based on a predetermined radius associated with the isometric point of a knee, said instrument being adapted for the reconstruction of the anterior cruciate of the knee by an extra-articular passage, and said hook is adapted to bear on a posterior edge of a femoral condyle, and said means including a passageway comprise an aimer barrel having a tunnel positioned therein, said tunnel having an inlet, an outlet and predetermined horizontal and vertical directions, said aimer barrel being guidable along a graduated scale, means for stopping said aimer barrel to obtain a distance between said outlet of said tunnel and said hook so that an axial direction of said tunnel from the external cortical of the femur to the inter-condyloid insertion area of the anterior cruciate intersects said rod at a point of intersection situated at a distance from the bearing surface of said hook which is equal to a predetermined radius associated with the isometric point of a knee.

11. The instrument according to claim 10, wherein said handle is positioned perpendicular to said rod and includes an end spaced from said rod, said handle including at said spaced end a passage positioned parallel to said rod, a bar slidable within said passage, screw means for locking said bar in a set position within said passage.

12. The instrument according to claim 11, wherein said bar includes on one end said aimer barrel and on an opposite end a graduated scale, and said aimer barrel and said graduated scale are related so as to obtain a desired intersection between an axis extending through said tunnel, said rod and said hook.

13. The instrument according to claim 12, wherein said axis has an angle of about 20° with said bar.

14. The instrument according to claim 13, wherein said bar is offset at an upward angle of 40° with respect to a horizontal plane passing through said rod and said hook.

15. The instrument according to claim 12, wherein said instrument is for drilling a transtibial tunnel and said aimer barrel has a longitudinal axis located in a plane passing through said rod and handle, and an end which is positioned at said bearing surface of said hook.

16. The instrument according to claim 12, wherein said aimer barrel includes means for permitting retention of bushes having a central guiding axis.

17. The instrument according to claim 16, wherein said means for permitting retention include an inside thread to receive threaded bushes.

18. Surgical ancillary instrument for setting up a two-bundle neo-ligament according to claim 10, wherein said means including a passageway comprise two aimer barrels positionable to obtain two femoral insertion tunnels placed on either side of the isometric point of the knee according to a line between centers in making an angle of 45° with the vertical.

* * * * *